(12) United States Patent
Favier et al.

(10) Patent No.: US 9,434,978 B2
(45) Date of Patent: Sep. 6, 2016

(54) **CULTURE MEDIUM FOR SCREENING OR ENRICHMENT OF METHICILLIN-RESISTANT *S. AUREUS***

(75) Inventors: Christine Favier, Marnes la Coquette (FR); Agnès Kammoun, Reze (FR)

(73) Assignee: BIO-RAD INNOVATIONS, Marnes la Coquette (FR)

( * ) Notice: Subject to any disclaimer, the term of this patent is extended or adjusted under 35 U.S.C. 154(b) by 0 days.

(21) Appl. No.: 13/519,161

(22) PCT Filed: Dec. 29, 2010

(86) PCT No.: PCT/EP2010/070883
§ 371 (c)(1),
(2), (4) Date: Sep. 5, 2012

(87) PCT Pub. No.: WO2011/080305
PCT Pub. Date: Jul. 7, 2011

(65) Prior Publication Data
US 2012/0322098 A1    Dec. 20, 2012

Related U.S. Application Data

(60) Provisional application No. 61/291,457, filed on Dec. 31, 2009.

(30) Foreign Application Priority Data

Dec. 31, 2009 (EP) .................................. 09306356

(51) Int. Cl.
*C12Q 1/14*    (2006.01)
(52) U.S. Cl.
CPC ...................... *C12Q 1/14* (2013.01)
(58) Field of Classification Search
None
See application file for complete search history.

(56) References Cited

U.S. PATENT DOCUMENTS

| | | | | |
|---|---|---|---|---|
| 5,364,767 A | * | 11/1994 | Flowers et al. | 435/39 |
| 5,716,799 A | * | 2/1998 | Rambach | 435/34 |
| 5,958,675 A | * | 9/1999 | Wicks et al. | 435/5 |
| 8,415,115 B2 | * | 4/2013 | Orenga et al. | 435/18 |
| 2006/0035309 A1 | | 2/2006 | Rambach et al. | |
| 2010/0035979 A1 | * | 2/2010 | Stapleton et al. | 514/456 |
| 2011/0165604 A1 | * | 7/2011 | Orenga et al. | 435/18 |
| 2011/0165614 A1 | * | 7/2011 | Orenga et al. | 435/36 |

FOREIGN PATENT DOCUMENTS

| | | | |
|---|---|---|---|
| WO | WO 2004/027086 | 4/2004 | |
| WO | WO 2004/063391 | 7/2004 | |
| WO | WO 2007/096639 | * 8/2007 | ............ C12Q 1/04 |

OTHER PUBLICATIONS

Lee et al., Curr. Op. Microbiol., 2(5):475-482 (1999).*
Wertheim, H. et al., "Improved Detection of Methicillin-Resistant *Staphylococcus aureus* Using Phenyl Mannitol Broth Containing Aztreonam and Ceftizoxime" *Journal of Clinical Microbiology*, Jul. 2001, pp. 2660-2662, vol. 39, No. 7.
Felten, A. et al. "Evaluation of Three Techniques for Detection of Low-Level Methicillin-Resistant *Staphylococcus aureus* (MRSA): a Disk Diffusion Method with Cefoxitin and Moxalactam, the Vitek 2 System, and the MRSA-Screen Latex Agglutination Test" *Journal of Clinical Microbiology*, Aug. 2002, pp. 2766-2771, vol. 40, No. 8.
Written Opinion in International Application No. PCT/EP2010/070883, Apr. 4, 2011, pp. 1-4.

* cited by examiner

*Primary Examiner* — Thomas J Visone
(74) *Attorney, Agent, or Firm* — Saliwanchik, Lloyd & Eisenschenk

(57) ABSTRACT

The invention relates to culture medium for screening or enrichment of methicillin-resistant *Staphylococcus aureus* (MRSA), which medium comprises a combination of at least two cephalosporins.

20 Claims, No Drawings

CULTURE MEDIUM FOR SCREENING OR ENRICHMENT OF METHICILLIN-RESISTANT S. AUREUS

CROSS-REFERENCE TO RELATED APPLICATIONS

This application is the U.S. national stage application of International Patent Application No. PCT/EP2010/070883, filed Dec. 29, 2010, which claims the benefit of U.S. Provisional Patent Application No. 61/291,457, filed Dec. 31, 2009.

The invention relates to the rapid identification or enrichment of methicillin-resistant *Staphylococcus aureus* (MRSA).

BACKGROUND OF THE INVENTION

*Staphylococcus aureus* is one of the most commonly identified pathogens in human medicine and is a major cause of nosocomial infections and community-acquired infections. Resistance to methicillin, reported for the first time in 1961, is now widespread in hospitals all over the world. The rapid and reliable identification of methicillin-resistant *Staphylococcus aureus* (MRSA) has become essential for appropriate patient care, and control of strain spreading.

A specific medium is optimal when it promotes the growth of the expected species and inhibits the growth of non-expected species. For the detection or enrichment of MRSA, it is critical to get all MRSA and to inhibit all MSSA, because both micro-organisms share identical phenotypic activities. For such a detection or enrichment medium, both sensitivity and specificity must be excellent.

The standard procedure for identifying MRSA is based on cultures using selective agar media (Cherkaoui et al, 2007, J. Med. Microbiol., 56:500-503).

International patent applications WO2004/027086 and WO2004/063391 disclose chromogenic agar media containing a β-lactam antibiotic, in particular a cephalosporin. Several chromogenic media for the screening of MRSA are commercially available. Cherkaoui et al, supra, compared the performance of four of them: oxacillin-resistance screening agar base (ORSAB; Oxoid), MRSA ID (BioMérieux); Chromogen oxacillin *S. aureus* (Axon Lab) and MRSASelect (Bio-Rad). Stoakes et al, 2006, J. Clin. Microbiol., 44(3):637-639) compared MRSASelect to CHROMagar MRSA (Becton-Dickinson), and mannitol-salt medium supplemented with oxacillin or cefoxitin (MSA-OXA and MSA-CFOX, Oxoid). However these media are not devoid of drawbacks.

Their stability is not warranted, since cephalosporins are known to be very unstable at room temperature or at higher temperature. For a commercial standpoint, it is important that the performances of the plates or tubes do not decrease during the shipping or delivery that can take several days usually at room temperature.

Furthermore, most of these media give a result after 18-24 h of incubation. To improve the sensitivity, the user often needs to extend the incubation time (generally 48 h), which leads to a delayed diagnosis and generally to a decreased specificity, particularly when the medium is not stable enough. It is also often recommended for the user to perform confirmation tests, such antimicrobial susceptibility testing, latex agglutination or PCR, which leads to an increased cost of the analysis and, once again, a delayed diagnosis. Therefore there is a continuing need to provide a MRSA detection medium with higher performance than the current chromogenic media in terms of sensitivity and/or specificity. Preferably such a medium should allow a rapid detection (within 18-24 h) and exhibit a good stability.

SUMMARY OF THE INVENTION

This invention provides a culture medium that meets these needs.

A subject of the invention is thus a culture medium for screening or enrichment of methicillin-resistant *Staphylococcus aureus* (MRSA), which medium comprises a combination of at least two cephalosporins.

In a preferred embodiment, the medium further comprises a chromogenic agent, which may be e.g. 6 chloro 3-indoxyl-phosphate.

In a preferred embodiment the culture medium is an agar culture medium. However it may also be a liquid culture medium, i.e. a broth.

In a particular embodiment, the medium comprises two cephalosporins.

In another particular embodiment, the medium comprises three cephalosporins.

The invention further provides a method for screening or enriching methicillin-resistant *Staphylococcus aureus* (MRSA) in a culture medium or broth, which method comprises (i) inoculating the culture medium defined herein, with bacteria to test, (ii) culturing said bacteria in said culture medium, and (iii) optionally identifying the presence of MRSA strains, which appear as colored colonies on the medium when the medium comprises a chromogenic agent.

In a particular embodiment, the bacteria to test are in the form of a clinical sample, such as a nasal swab.

DETAILED DESCRIPTION OF THE INVENTION

The inventors hypothesized that in the long run stability of an MRSA culture medium comprising a cephalosporin could be improved by adding a second cephalosporin in the medium. Surprisingly enough, they found out that adding another cephalosporin made it possible not only to indeed improve stability of the culture medium, but also to increase its specificity in the long run.

For a commercial point of view it is important that the performances of the plates or tubes do not decrease during the shelf life of the product due to shipping/delivery conditions that can take several days. The mix of cephalosporins unexpectedly increased the robustness or stability of the medium as observed by the performances obtained after thermal stress (when plates were placed on an incubator for 3 days at 37° C.).

The mix of cephalosporins further limited the growth of false-positive colonies keeping an optimal sensitivity.

A subject of the invention is a culture medium for screening or enrichment of methicillin-resistant *Staphylococcus aureus* (MRSA), which medium comprises a combination of at least two cephalosporins.

Examples of cephalosporins include, but are not limited to, any first, second, third and fourth generation cephalosporin.

The expression "second or third generation cephalosporin" is intended to denote the antibiotics of the cephalosporin family having a formula derived from formula (I) below:

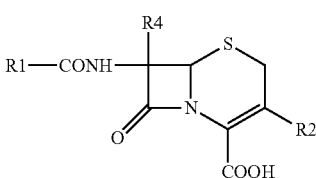

in which R2 is an H group, an acetoxymethyl group, a methylthiotetrazol group, a dimethylaminoethylthio-tetrazol group, a triazine group, an acetaminopyridine (pyridinium) group, or a pyridinium group substituted with a carbamoyl group, a cyclopentopyridinium group or a thiomethylacetoxythiazol group, R1 is an amino-2-thiazole heterocycle, an alpha-piperazinedione or an alpha-sulfophenyl, and R4 is an H group or an alpha-methoxy radical.

In particular, the compounds having the formula below:

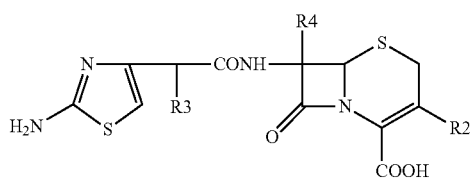

in which R3 is an H group or an alpha-methoxyimino group, are intended to be denoted. In a particular case, the R4 group is hydrogen.

Cephamycins are compounds in which the R4 group is an alpha-methoxy radical, protecting the beta-lactam ring against hydrolysis by beta-lactamases, and correspond to the formula below:

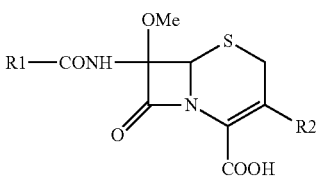

Oxacephems are compounds in which the sulfur atom of the cephem ring is replaced with an oxygen atom, and are considered to be derivatives of formula (I) given above.

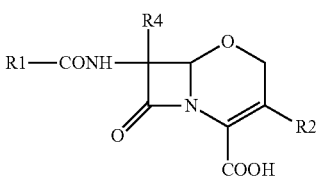

In general, for these compounds, the R4 group is an [alpha]-methoxy.

A definition of the cephalosporins thus envisioned can be found in Binger "Mécanisme d'Action des Bêta-lactamines, (de la structure bactérienne à la structure de la molecule)" 1986, Roussel (Paris) publisher, chapter III, pages 47-62, and chapter IV, pages 63-68), and in the work by Richmond (Beta-lactam antibiotics (the background to their use as therapeutic aents), Hoechst Aktiengesellschaft, D-6230 Frankfurt (Main) 80 publisher, 1981, chapter 3, pages 55-65).

Among the second and third generation cephalosporins, mention may be made of: loracarbef, cefaclor, cefuroxime, cefprozil, cefoxitin (cefoxitan), cefamandole, cefotian, cefotetan, cefmetazole, cefocinide, cefora nide, cefpodoxime, cefixime, cefotaxime, ceftizoxime, ceftriaxone, ceftazidime, cefmenoxime, cefodizime, cefoperazone, cefepime (sometimes classified as a fourth generation cephalosporin), cefpirome, cefsulfonide, cefetamete, ceftibutene, moxalactam (latamoxef) and flomoxef, in particular in the form of salts (e.g. sodium salts).

In particular, cephalosporins may be chosen from the group of cephamycins (including e.g. cefoxitin, cefotetan, cefmetazole, cefbutperazone, cefminox) and of oxacephems (including e.g. moxalactam or flomoxef).

Preferably said cephalosporins are selected from the group consisting of cefotetan (CU), ceftriaxone (CRO), cefuroxime (CXM), cefsulodin (CFS), ceftibuten (CTB), cefepime (FEP), cefoperazone (CFP), cefpodoxime (CPD), cefoxitine (FOX), flomoxef, cefmetazole (CMT), moxalactam (MOX) and ceftiofur (XLN), or salts thereof. Hereinafter, reference is made either to the complete name of the cephalosporin or the 3 letter abbreviation.

More preferably, the medium comprises a combination of cephalosporins selected in the group consisting of:
cefotetan and ceftriaxone;
cefotetan and cefoxitin;
cefotetan and cefpodoxime;
cefpodoxime and cefsulodin;
cefuroxime and cefsulodin;
cefsulodin and cefotetan;
cefsulodin and ceftriaxone;
ceftiofur and cefsulodin;
cefsulodin and cefepime;
moxalactam and cefoxitin;
moxalactam and cefpodoxime;
cefotetan and ceftiofur;
cefpodoxime and ceftriaxone;
cefoperazone and ceftiofur;
cefoperazone and cefsulodin;
ceftriaxone and cefoperazone;
cefoperazone and cefuroxime;
cefotetan and ceftibuten;
ceftriaxone and ceftibuten;
and
ceftriaxone and cefepime.

A "culture medium" as described herein is a nutritive agar medium or a liquid medium (i.e. a broth) that contains nutrients allowing *Staphylococcus aureus* to grow. Culture media for *S. aureus* are commonly known, and generally contain meat extracts and peptone, as well as salts (see for instance WO2004/027086).

The term "screening" or "screening MRSA" refers to the detection and/or identification of MRSA, and involves promoting the growth and distinguishing MRSA from other *S. aureus* and other bacteria.

The term "enrichment" or "enriching MRSA" refers to the selective culture of MRSA and involves promoting the growth of MRSA over the growth of from other *S. aureus* and other bacteria.

The culture medium is inoculated with bacteria to test or directly with a biological or environmental sample. The bacteria to test may be from human clinical sources or from any source including but not limited to food, living or dead animal or plant tissue, water, air, other inanimate environmental surfaces. If the source of the sample is solid, the sample may be suspended in a liquid diluent prior to inoculation of the culture medium. Also, a liquid or liquefied sample may be diluted prior to inoculating the culture medium. In certain embodiments, the sample may be serially diluted and the serial dilutions used to inoculate a plurality of culture media in order to obtain a more precise enumeration of S. aureus in the original sample. In a preferred embodiment, the bacteria to test are in the form of a clinical sample, such as a nasal swab, a wound sample or a blood culture.

The term "stability" refers to the ability of the medium according to the invention to allow the selective screening or detection of MRSA for a given period of time, with the same reliability throughout said period of time.

The inoculated culture medium is incubated under conditions that permit the growth of staphylococci. In one embodiment of the method of the present invention, the inoculated culture medium is incubated at 37° C. for about 24 hours. However, in other embodiments, the inoculated culture medium may be incubated from about 18 hours to about 48 hours at about 30° C. to about 42° C. In particular, the incubation temperature is from about 33° C. to 39° C. Although supplementation with additional NaCl, up to a concentration of about 5%, produce optimal results, concentrations as low as 2.5% NaCl also perform well. Concentrations as low as 0.01% may also provide satisfactory results.

The concentration of each cephalosporin in the medium according to the invention is preferably between 0.01 and 50 mg/l, preferably 0.5 and 30 mg/l, in particular 0.5 and 15 mg/l, still preferably between 0.5 mg/l and 10 mg/l. In a particular embodiment, the culture medium comprises from 1 to 2 or 2.5 mg/l of cefotetan and from 1.5 to 2.5 mg/l of ceftriaxone, preferably 1.75 mg/l, 2 mg/l or 2.4 mg/l cefotetan and 2.4 mg/l ceftriaxone.

In another particular embodiment, the culture medium comprises from 1.5 to 2.5 mg/l of cefotetan and from 1.5 to 2.5 mg/l of cefpodoxime, preferably 2 mg/l cefotetan and 1.5 mg/l cefpodoxime.

The culture medium preferably comprises a chromogenic agent, and the cultured microorganisms that survive produce a detectable colored colony in or on the medium, indicating the microorganisms' growth and permitting the specific detection of S. aureus (the methicillin resistant Staphylococci epidermidis growing on the medium as white colonies).

The media according to the present invention preferably contain from 0.01 to 0.50 g/l, in particular from 0.05 to 0.40 g/l of chromogenic agent that allows the coloration of the strains of Staphylococcus aureus. The chromogenic agent is preferably 6 chloro 3-indoxyl phosphate. Other examples of chromogenic agents that can be used in the medium according to the invention include, but are not limited to, 5-bromo-6-chloro-3-indoxyl phosphate, 5-bromo-4-chloro-3-indoxyl-phosphate, 5-bromo-3-indoxyl-phosphate, 3-indoxyl-phosphate, 6-bromo-3-indoxyl-α-D-glucoside, 5-bromo-4-chloro-3-indoxyl-α-D-glucoside, 5-bromo-4-chloro-3-indoxyl-N-methyl-α-D-glucoside, 6-Chloro-3-indoxyl-α-D-glucoside.

In a preferred embodiment, in addition to the chromogenic agent mentioned above the medium according to the invention comprises at least one additional chromogenic agent that allows the coloration of other microorganisms that could be present in the inoculum, such as 5-bromo-4-chloro-3-indoxyl glucuronide ("X-glucuronide") and/or 5-bromo-4-chloro-3-indoxyl glucoside ("X-glu"),5-bromo-4-chloro-3-indoxyl galactoside ("X-gal"). The medium according to the invention may also comprise a fluorogenic agent such as 4-Methylumbelliferyl-α-D-glucoside.

The culture medium of the invention may comprise other antibiotics, such as vancomycine, teicoplanine, avoparcine. Preferably the culture medium does not comprise oxacillin and/or does not comprise cefoxitin.

The culture medium of the invention is very sensible. It allows for identification of weakly resistant MRSA strains and provides a good specificity.

Preferably the medium comprises any of the following combinations of cephalosporins (it is to be understood the each concentration can be applied at +/−10%):

CTT 2 mg/l+CRO 2 mg/l
CTT 2.4 mg/l+CRO 2.4 mg/l
FOX 4.5 mg/l+CTT 2 mg/l
CTT 2 mg/l+CPD 1.5 mg/l
CTT 2.4 mg/l+CPD 1.8 mg/l
CPD 1.5 mg/l+CFS 3.5 mg/l
CXM 0.75 mg/l+CFS 3 mg/l
CXM 0.75 mg/l+CFS 3.5 mg/l
CFS 3.5 mg/l+CRO 2 mg/l
XLN 0.75 mg/l+CFS 3 mg/l
CFS 3 mg/l+FEP 2 mg/l
MOX 6 mg/l+FOX 4.5 mg/l
MOX 4 mg/l+CPD 1 mg/l
CTT 2 mg/l+XLN 0.75 mg/l
CTT 1.75 mg/l+CXM 0.75 mg/l
CPD 2.5 mg/l+CRO 3.5 mg/l
CPD 2 mg/l+CRO 4 mg/l
CFP 1.75 mg/l+XLN 2 mg/l
CFP 2.25 mg/l+XLN 1.25 mg/l
CFP 1.5 mg/l+CFS 3 mg/l

The media of the invention show an excellent performance in terms of sensitivity and specificity. Optimal media were shown to be both sensitive and specific when tested within 24 h. Some others performed better when tested within 48 h. However the delay in diagnosing was balanced by an excellent stability.

The media of the invention showed a good selectivity. Indeed, the growth of other staphylococci (i.e. non-aureus), mainly methicillin resistant S. epidermidis, can be an issue, because some of them are likely to give a false-positive reaction and then be classified as MRSA. The mix of cephalosporins according to the invention makes it possible to inhibit these undesired species or to limit their coloration.

In a preferred embodiment, the culture medium according to the invention comprises a compound that inhibits the growth of Staphylococcus epidermidis without inhibiting Staphylococcus aureus. Preferably, said compound is deferoxamine, which is preferably used in a concentration of 0.01 to 0.10 g/l. Preferably said compound is cefoperazone. Indeed the inventors have shown that the addition of cefoperazone in a medium containing already at least one other cephalosporin (to select the MRSA and inhibit the MSSA) advantageously reduces the coloration or inhibits the growth of methicillin resistant S. epidermidis, reducing the risk of false positive results. Preferably, cefoperazone is used at a concentration from 0.1 to 3 mg/l.

In still a preferred embodiment, the culture medium comprises three cephalosporins, including cefoperazone.

In a most preferred embodiment, the culture medium comprises cefotetan, ceftriaxone and cefoperazone.

The below examples illustrate the invention without limiting its scope.

EXAMPLES

Example 1

Comparison of Performance of a Culture Medium Using a Cephalosporin vs. Cephalosporins in Combination Materials & Methods The basal medium comprises peptone, salts, antifungal and antibacterial agents to inhibit the growth of Gram negative bacteria and fungi. The basal medium is chosen to promote the growth of *staphylococci*, in particular *Staphylococcus aureus*.

Several strains of MRSA (methicillin resistant *S. aureus*) and MSSA (methicillin susceptible *S. aureus*) have been chosen from a collection of strains. Strains were cultivated first on a non selective medium. The colonies are used to perform a "heavy inoculum or HI", corresponding to approximately $10^8$ bacteria/mL inoculated as a spot on a small portion of the plate, and a "light inoculum or LI", corresponding to approximately $10^5$ bacteria/mL streaked on a large portion of the plate. Plates were incubated for 48 h at 35-37° C. The reading was performed at 24 and 48 h of incubation time.

Abbreviations and legends to the Tables:
cefotetan (CTT)
ceftriaxone (CRO)
cefuroxime (CXM)
cefsulodin (CFS),
Cefepime (FEP)
Cefoperazone (CFP)
cefpodoxime (CPD)
moxalactam (MOX)
cefoxitin (FOX)
cefmetazole (CMT)
ceftiofur (XLN)
G: growth (if nothing else is written, "G" means growth with HI and LI at 24 h); Imp G: heavy growth; AG: absence of growth; cfu: colony forming unit; μcfu: pinpoint colonies; SENS: Sensitivity (%); SPE: Specificity (%); MRSA: methicillin-resistant *Staphylococcus aureus*; MSSA: methicillin-sensitive *Staphylococcus aureus*; MRSE: methicillin-resistant *Staphylococcus epidermidis*; MSSE: methicillin-sensitive *Staphylococcus epidermidis;*

Results

The below Tables show the performance of various formulas, containing a single cephalosporin or a mixture of cephalosporins. The best media provide growth and coloration of MRSA without growth of MSSA.

TABLE 1

Performance of a medium with a single cephalosporin (antibiotic concentration in mg/L)

| Strains | CTT, 15 mg/L | CTT, 17 mg/L |
| --- | --- | --- |
| Experiment # | 17 | 18 |
| MRSA 653130502 | G | G |
| MRSA 599190802 R | G | G of colorless cfu |
| MRSA 1.1.8 | G | G |
| MRSA 5030 | G with HI at 24 h; G with LI at 48 h | Trace at 24 h; G only with HI at 48 h |
| MRSA ATCC 43300 | G | G |
| MRSA FOX 684 RDC 77 | G with HI + 1 cfu with LI at 24 h | G only with HI at 24 h; with HI + LI at 48 h |
| MSSA 1.1.2 | 1cfu at 24 h; G at 48 h | AG |
| MSSA M366806 | G | AG |
| MSSA M366930 | AG | AG |
| MSSA 4007 | G | G at 48 h |
| MSSA96019 | G | AG |
| MSSA ATCC 25923 | AG | AG |
| MSSA 3890 | AG | AG |
| MSSA 93096 | AG | AG |
| Sensitivity (24 h) | 100 | 67 |
| Specificity (24 h) | 50 | 100 |
| Sensitivity (48 h) | 100 | 100 |
| Specificity (48 h) | 50 | 88 |
| SENS + SPE 24 h | 150 | 167 |
| SENS + SPE 48 h | 150 | 188 |
| TOTAL | 300 | 355 |

CTT, 17 mg/L, was chosen as the best concentration to obtain the most satisfying, albeit not ideal, balance in sensitivity and specificity. For each molecule used alone, the best compromise between sensitivity and specificity has been chosen.

TABLE 2

Performance of CRO + CTT

| Strains | CRO 5 mg/L | CTT 17 mg/L | CRO 2 mg/L + CTT 2 mg/L |
| --- | --- | --- | --- |
| Experiment # | 18 | 18 | 18 |
| MRSA 653130502 | G | G | G |
| MRSA 599190802 R | G of colorless cfu | G of colorless cfu | G |
| MRSA 1.1.8 | G | G | G |
| MRSA 5030 | G only with HI at 24 h; G at 48 h | Trace at 24 h; G only with HI at 48 h | G |
| MRSA ATCC 43300 | G of colorless cfu | G | G |
| MRSA FOX 684 RDC 77 | G only with HI at 24 h; HI + LI at 48 h | G only with HI at 24 h; with HI + LI at 48 h | G |
| MSSA 1.1.2 | G at 48 h | AG | AG |
| MSSA M366806 | AG | AG | AG |
| MSSA M366930 | AG | AG | AG |
| MSSA 4007 | 1 CFU at 48 h | G at 48 h | AG |
| MSSA96019 | G at 48 h | AG | AG |
| MSSA ATCC 25923 | AG | AG | AG |
| MSSA 3890 | G at 48 h | AG | AG |
| MSSA 93096 | AG | AG | AG |
| Sensitivity (24 h) | 67 | 67 | 100 |
| Specificity (24 h) | 100 | 100 | 100 |
| Sensitivity (48 h) | 100 | 100 | 100 |
| Specificity (48 h) | 50 | 88 | 100 |
| SENS + SPE 24 h | 167 | 167 | 200 |
| SENS + SPE 48 h | 150 | 188 | 200 |
| TOTAL | 317 | 355 | 400 |

With CRO used alone, the MRSA colonies were colorless, and MSSA were able to grow. With CTT used alone, MSSA strains grew, while some MRSA did not grow optimally.

With the mix of CRO and CTT, all MRSA were able to grow, and no growth of MSSA was observed (100% sensitivity and 100% specificity at 24 h and 48 h).

TABLE 3

Performance of CTT + CPD

| Strains | CTT 17 mg/L | CPD 6 mg/L | CTT 2 mg/L + CPD 1.5 mg/L |
|---|---|---|---|
| Experiment # | 18 | 18 | 18 |
| MRSA 653130502 | G | G | G |
| MRSA 599190802 R | G of colorless cfu | G | G |
| MRSA 1.1.8 | G | G | G |
| MRSA 5030 | Trace at 24 h; G only with HI at 48 h | AG at 24 h; 4 CFU with HI at 48 h | 1 cfu with HI at 48 h |
| MRSA ATCC 43300 | G | G | G |
| MRSA FOX 684 RDC 77 | G only with HI at 24 h | G only with HI at 24 h | G |
| MSSA 1.1.2 | AG | G at 48 h | AG |
| MSSA M366806 | AG | AG | AG |
| MSSA M366930 | AG | AG | AG |
| MSSA 4007 | G at 48 h | AG | AG |
| MSSA96019 | AG | AG | AG |
| MSSA ATCC 25923 | AG | AG | AG |
| MSSA 3890 | AG | AG | AG |
| MSSA 93096 | AG | AG | AG |
| Sensitivity (24 h) | 67 | 83 | 83 |
| Specificity (24 h) | 100 | 100 | 100 |
| Sensitivity (48 h) | 100 | 100 | 100 |
| Specificity (48 h) | 88 | 88 | 100 |
| SENS + SPE 24 h | 167 | 183 | 183 |
| SENS + SPE 48 h | 188 | 188 | 200 |
| TOTAL | 355 | 371 | 383 |

With CTT used alone, MSSA strains grew, while some MRSA did not grow well.

With CPD used alone, MSSA strains grew, while some MRSA did not grow optimally. No optimal concentration could be found.

With the mix of CTT and CPD, all MRSA were able to grow at 48 h, and no growth of MSSA was observed (100% sensitivity and 100% specificity at 48 h).

TABLE 4

Performance of CXM + CFS

| Strains | CXM 2 mg/L | CFS 6 mg/L | CXM 0.75 mg/L + CFS 3 mg/L |
|---|---|---|---|
| Experiment # | 17 | 17 | 17 |
| MRSA 653130502 | G | G | G |
| MRSA 599190802 R | G | G of pinpoint colourless cfu | G |
| MRSA 1.1.8 | G | G of pinpoint colourless cfu | G |
| MRSA 5030 | AG | G with HI at 24 h Trace with LI at 24 h; G at 48 h | AG |
| MRSA ATCC 43300 | Trace of colourless pinpoint cfu at 24 h | G | G |
| MRSA FOX 684 RDC 77 | G only with HI | Trace with HI, 1 colorless cfu with LI | G only with HI |
| MSSA 1.1.2 | G | 1cfu at 24 h; G at 48 h | 1cfu at 24 or 48 h |
| MSSA M366806 | AG | G at 48 h | AG |
| MSSA M366930 | AG | 1cfu | AG |
| MSSA 4007 | AG | G at 48 h | AG |
| MSSA96019 | G | G at 48 h | AG |
| MSSA ATCC 25923 | AG | AG | AG |
| MSSA 3890 | G at 48 h | AG | AG |
| MSSA 93096 | AG | G at 48 h | AG |
| Sensitivity (24 h) | 67 | 50 | 83 |
| Specificity (24 h) | 75 | 75 | 87 |
| Sensitivity (48 h) | 83 | 100 | 83 |
| Specificity (48 h) | 63 | 25 | 87 |
| SENS + SPE 24 h | 142 | 125 | 170 |
| SENS + SPE 48 h | 146 | 125 | 170 |
| TOTAL | 288 | 250 | 340 |

With CXM or CFS used alone, MSSA strains grew, while some MRSA did not grow optimally. No optimal concentration could be found.

With the mix of CXM and CFS, all MRSA but one were able to grow, and only one cfu of MSSA was observed.

TABLE 5

Performance of CRO + CFS

| Strains | CRO 5 mg/L | CFS 6 mg/L | CRO 2 mg/L + CFS 3.5 mg/L |
|---|---|---|---|
| Experiment # | 18 | 18 | 18 |
| MRSA 653130502 | G | G | G |
| MRSA 599190802 R | G | G | G |
| MRSA 1.1.8 | G | G colorless cfu | G |
| MRSA 5030 | G only with HI at 24 h; G at 48 h | G with HI & trace with LI at 24 h; G at 48 h | Trace with HI at 24 h G with HI + LI at 48 h |
| MRSA ATCC 43300 | G | G | G |
| MRSA FOX 684 RDC 77 | G with HI at 24 h; G at 48 h | Only 1cfu with HI at 24 h G with HI + 2 cfu only with LI at 48 h | G with HI at 24 h; G with HI + LI at 48 h |
| MSSA 1.1.2 | G at 48 h | G at 48 h | AG |
| MSSA M366806 | AG | G at 48 h | AG |

TABLE 5-continued

Performance of CRO + CFS

| Strains | CRO 5 mg/L | CFS 6 mg/L | CRO 2 mg/L + CFS 3.5 mg/L |
|---|---|---|---|
| MSSA M366930 | AG | G at 48 h | AG |
| MSSA 4007 | 1 CFU at 48 h | G | AG |
| MSSA96019 | G at 48 h | G at 48 h | AG |
| MSSA ATCC 25923 | AG | AG | AG |
| MSSA 3890 | G at 48 h | G at 48 h | AG |
| MSSA 93096 | AG | G at 48 h | AG |
| Sensitivity (24 h) | 67 | 83 | 83 |
| Specificity (24 h) | 100 | 88 | 100 |
| Sensitivity (48 h) | 100 | 100 | 100 |
| Specificity (48 h) | 50 | 13 | 100 |
| SENS + SPE 24 h | 167 | 171 | 183 |
| SENS + SPE 48 h | 150 | 113 | 200 |
| TOTAL | 317 | 284 | 383 |

With CRO used alone, MSSA were able to grow.

With CFS used alone, MSSA strains grew, while some MRSA did not grow optimally. No optimal concentration could be found.

With the mix of CRO and CFS, all MRSA were able to grow, and no growth of MSSA was observed.

TABLE 6

Performance of FEP + CFS

| Strains | FEP 5 mg/L | CFS 6 mg/L | FEP 2 mg/L + CFS 3 mg/L |
|---|---|---|---|
| Experiment # | 18 | 18 | 18 |
| MRSA 653130502 | G colorless cfu | G | G |
| MRSA 599190802 R | G white cfu | G | G |
| MRSA 1.1.8 | G | G colorless cfu | G |
| MRSA 5030 | G only with HI | G with HI & trace with LI at 24 h; G at 48 h | 2 pinpoint cfu with HI at 24 h Growth with HI at 48 h |
| MRSA ATCC 43300 | G colorless cfu | G | G |
| MRSA FOX 684 RDC 77 | AG at 24 h; G 48 h | 1cfu with HI at 24 h G with HI + 2 cfu only with LI at 48 h | Trace with HI at 24 h; G 48 h |
| MSSA 1.1.2 | G | G at 48 h | AG |
| MSSA M366806 | AG | G at 48 h | AG |
| MSSA M366930 | AG | G at 48 h | AG |
| MSSA 4007 | AG | G | AG |
| MSSA96019 | G | G at 48 h | AG |
| MSSA ATCC 25923 | AG | AG | AG |
| MSSA 3890 | G | G at 48 h | AG |
| MSSA 93096 | AG | G at 48 h | AG |
| Sensitivity (24 h) | 33 | 83 | 67 |
| Specificity (24 h) | 63 | 88 | 100 |
| Sensitivity (48 h) | 100 | 100 | 100 |
| Specificity (48 h) | 63 | 13 | 100 |
| SENS + SPE 24 h | 96 | 171 | 167 |
| SENS + SPE 48 h | 163 | 113 | 200 |
| TOTAL | 259 | 284 | 367 |

With FEP used alone, some MRSA did not grow well, while MSSA strains grew. No optimal concentration could be found.

With CFS used alone, MSSA strains grew, while some MRSA showed difficulty to grow. No optimal concentration could be found.

With the mix of FEP and CFS, all MRSA were able to grow at 48 h, and no growth of MSSA was observed.

TABLE 7

Performance of CTT + XLN

| Strains | CTT 17 mg/L | XLN 2 mg/L | CTT 2 mg/L + XLN 0.75 mg/L |
|---|---|---|---|
| Experiment # | 18 | 18 | 18 |
| MRSA 653130502 | G | G of pinpoint colorless cfu | G |
| MRSA 599190802 R | G of colorless cfu | G of pinpoint white cfu | G |
| MRSA 1.1.8 | G | G | G |
| MRSA 5030 | Trace at 24 h; G only with HI at 48 h | Trace pinpoint colorless cfu at 24 h; G with HI at 48 h + 1cfu with LI | 3 colored cfu on the spot at 24 h; G with HI at 48 h |
| MRSA ATCC 43300 | G | G of colorless cfu | G |
| MRSA FOX 684 RDC 77 | G only spot at 24 h; with HI + LI at 48 h | No growth at 24 h (trace); G with HI 9cfu at 48 h with LI | G |

TABLE 7-continued

Performance of CTT + XLN

| Strains | CTT 17 mg/L | XLN 2 mg/L | CTT 2 mg/L + XLN 0.75 mg/L |
|---|---|---|---|
| MSSA 1.1.2 | AG | Trace at 24 h; little G at 48 h | AG |
| MSSA M366806 | AG | AG | AG |
| MSSA M366930 | AG | AG | AG |
| MSSA 4007 | G at 48 h | AG | AG |
| MSSA96019 | AG | G at 24 h | AG |
| MSSA ATCC 25923 | AG | AG | AG |
| MSSA 3890 | AG | AG | AG |
| MSSA 93096 | AG | AG | AG |
| Sensitivity (24 h) | 67 | 17 | 100 |
| Specificity (24 h) | 100 | 100 | 100 |
| Sensitivity (48 h) | 100 | 100 | 100 |
| Specificity (48 h) | 88 | 88 | 100 |
| SENS + SPE 24 h | 167 | 117 | 200 |
| SENS + SPE 48 h | 188 | 166 | 200 |
| TOTAL | 355 | 283 | 400 |

With CTT used alone, MSSA strains grew, while some MRSA did not grow enough to be detected.

With XLN used alone, MSSA strains grew, while some MRSA did not grow. No optimal concentration could be found.

With the mix of CTT and XLN, all MRSA were able to grow at 48 h, and no growth of MSSA was observed (100% sensitivity and 100% specificity).

TABLE 8

Performance of CXM + CTT

| Strains | CXM 2 mg/L | CTT 17 mg/L | CXM 0.75 mg/L + CTT 1.75 mg/L |
|---|---|---|---|
| Experiment # | 18 | 18 | 18 |
| MRSA 653130502 | G | G | G |
| MRSA 599190802 R | G of colorless cfu | G of colorless cfu | G |
| MRSA 1.1.8 | G | G | G |
| MRSA 5030 | Trace at 24 h; G only with HI at 48 h | Trace at 24 h; G only with HI at 48 h | AG |
| MRSA ATCC 43300 | AG | G | G |
| MRSA FOX 684 RDC 77 | G only spot at 24 h | G only spot at 24 h | G |
| MSSA 1.1.2 | Trace at 24 h; G at 48 h | AG | AG |
| MSSA M366806 | AG | AG | AG |
| MSSA M366930 | AG | AG | AG |
| MSSA 4007 | AG | G at 48 h | AG |
| MSSA96019 | Trace at 24 h; G at 48 h | AG | AG |
| MSSA ATCC 25923 | AG | AG | AG |
| MSSA 3890 | AG | AG | AG |
| MSSA 93096 | AG | AG | AG |
| Sensitivity (24 h) | 50 | 67 | 83 |
| Specificity (24 h) | 100 | 100 | 100 |
| Sensitivity (48 h) | 83 | 100 | 83 |
| Specificity (48 h) | 75 | 88 | 100 |
| SENS + SPE 24 h | 150 | 167 | 183 |
| SENS + SPE 48 h | 158 | 188 | 183 |
| TOTAL | 308 | 355 | 366 |

With CTT used alone, MSSA strains grew, while some MRSA did not grow well.

With CXM used alone, MSSA strains grew, while some MRSA did not grow. No optimal concentration could be found.

With the mix of CTT and CXM, all MRSA but one were able to grow at 48 h, and no growth of MSSA was observed.

Example 2

Stability Studies

When two cephalosporins are added, the stability of the formula is increased. Due to the fact that the molecules are unstable, growth of MSSA often appears after stress. The inventors have mimicked the stress due to transportation of the Petri dishes to the customer's lab, in summer, by placing the plates for 3 days at 37° C. before inoculation and incubation 24 or 48 h. The basal medium composition was the same as described in Example 1. Abbreviations have the same meaning.

The optimal concentration was chosen for Fox and Mox. Then inhibition of MSSA was observed (Table 9A).

TABLE 9A

Stability of FOX + MOX (24 h of incubation)

| Strains | FOX 6 mg/L | MOX 14 mg/L | FOX 4.5 mg/L + MOX 6 mg/L | FOX 6 mg/L STRESSED | MOX 14 mg/L STRESSED | FOX 4.5 mg/L + MOX 6 mg/L STRESSED |
|---|---|---|---|---|---|---|
| Experiment # | 17 | 17 | 17 | 18 | 18 | 18 |
| MRSA 653130502 | G | G | G | | | |

TABLE 9A-continued

Stability of FOX + MOX (24 h of incubation)

| Strains | FOX 6 mg/L | MOX 14 mg/L | FOX 4.5 mg/L + MOX 6 mg/L | FOX 6 mg/L STRESSED | MOX 14 mg/L STRESSED | FOX 4.5 mg/L + MOX 6 mg/L STRESSED |
|---|---|---|---|---|---|---|
| MRSA 599190802 R | G | G | G | | | |
| MRSA 1.1.8 | G | G | G | | | |
| MRSA ATCC 43300 | G | G | G | | | |
| MRSA FOX 684 RDC 77 | G | G | G | | | |
| MSSA 1.1.2 | AG | AG | AG | Imp G | AG | Trace |
| MSSA M366806 | AG | AG | AG | G | Imp G | G |
| MSSA M366930 | AG | AG | AG | Imp G | Imp G | AG |
| MSSA 4007 | AG | AG | AG | AG | Imp G | AG |
| MSSA96019 | AG | AG | AG | G | G | AG |
| MSSA ATCC 25923 | AG | AG | AG | AG | AG | AG |
| MSSA 3890 | AG | AG | AG | AG | AG | AG |
| MSSA 93096 | AG | AG | AG | AG | AG | AG |

With an optimal concentration of FOX, the molecule being used alone, 4 MSSA strains grew at 24 h after stress.

With an optimal concentration of MOX used alone, 4 MSSA strains grew at 24 h after stress.

With FOX+MOX combined, 1 MSSA only grew at 24 h after stress.

The inventors herein show that the growth of MSSA is still inhibited after stress and is less important with a mix of cephalosporins when compared to a cephalosporin used alone.

Additional experiments were performed with a combination of CTT and CPD (Table 9B), or a combination of CTT and CRO (Table 9C).

CTT, 22 mg/L, was eventually chosen as an optimal concentration to obtain the most satisfying, albeit not ideal, balance in sensitivity and specificity, when used alone.

CPD, 4 mg/L, was eventually chosen as an optimal concentration to obtain the most satisfying, albeit not ideal, balance in sensitivity and specificity, when used alone.

CRO, 4.5 mg/L, was chosen as the best concentration to obtain the most satisfying, albeit not ideal, balance in sensitivity and specificity, when used alone.

In tables 9B and 9C,

LG means "limited growth" for MRSA, i.e., growth only with a heavy inoculum (HI); no growth with the light inoculum (LI).

TABLE 9B

Stability of CTT + CPD (24 h of incubation)

| Strains | CTT 22 mg/L | CPD 4 mg/L | CTT 2.5 mg/L + CPD 1.8 mg/L | CTT 22 mg/L STRESSED | CPD 4 mg/L STRESSED | CTT 2.5 mg/L + CPD 1.8 mg/L STRESSED |
|---|---|---|---|---|---|---|
| Experiment # | 71 | 71 | 71 | 71 | 71 | 71 |
| MRSA 653130502 | G | G | G | G | G | G |
| MRSA 599190802 R | G | G | G | G | G | G |
| MRSA 1.1.8 | G | G | G | G | G | G |
| MRSA 5030 | LG | LG | LG | G | LG | LG |
| MRSA ATCC 43300 | G | G | G | G | G | G |
| MRSA FOX 684 RDC 77 | LG | LG | LG | LG | LG | LG |
| MSSA 1.1.2 | AG | G | AG | G (colorless) | G | AG |
| MSSA M366806 | AG | AG | AG | G | AG | AG |
| MSSA M366930 | AG | AG | AG | G | AG | AG |
| MSSA 4007 | G | AG | AG | G | AG | AG |
| MSSA96019 | AG | G | AG | G | G | AG |

TABLE 9B-continued

Stability of CTT + CPD (24 h of incubation)

| Strains | CTT 22 mg/L | CPD 4 mg/L | CTT 2.5 mg/L + CPD 1.8 mg/L | CTT 22 mg/L STRESSED | CPD 4 mg/L STRESSED | CTT 2.5 mg/L + CPD 1.8 mg/L STRESSED |
|---|---|---|---|---|---|---|
| MSSA ATCC 25923 | AG | AG | AG | AG | AG | AG |
| MSSA 3890 | AG | AG | AG | G (colorless) | AG | AG |
| MSSA 93096 | AG | AG | AG | G | AG | AG |

In control plates with CTT or CPD only, not submitted to any stress, all MRSA grew, when few strains of MSSA were able to grow at 24 h.

In plates combining CTT and CPD, but not submitted to stress, all MRSA grew and no MSSA was able to grow.

All MRSA grew, and the majority of MSSA strains was also able to grow at 24 h in plates with CTT submitted to stress (for 3 days at 37° C. before inoculation). There was a dramatic decrease in specificity in comparison with the control (not stressed) plates.

All MRSA grew, and two MSSA strains were also able to grow at 24 h in plates with CPD submitted to stress (for 3 days at 37° C. before inoculation).

In plates combining CTT and CPD, submitted to stress, all MRSA grew and no MSSA was able to grow.

The mixture of antibiotics thus gave the best performance and showed the best stability after stress.

stress (for 3 days at 37° C. before inoculation). There was a dramatic decrease in specificity in comparison with the control (not stressed) plates.

All MRSA grew, and four MSSA strains were also able to grow at 24 h in plates with CRO submitted to stress (for 3 days at 37° C. before inoculation). There was a decrease of specificity in comparison with the control (not stressed) plates.

In plates combining CTT and CRO, submitted to stress, all MRSA grew and only one MSSA was able to grow at 24 h.

The mixture of antibiotics thus gave the best performance and showed the best stability after stress.

TABLE 9C

Stability of CTT + CRO (24 h of incubation)

| Strains | CTT 22 mg/L | CRO 4.5 mg/L | CTT 2.4 mg/L + CRO 2.4 mg/L | CTT 22 mg/L STRESSED | CRO 4.5 mg/L STRESSED | CTT 2.4 mg/L + CRO 2.4 mg/L STRESSED |
|---|---|---|---|---|---|---|
| Experiment # | 71 | 71 | 71 | 71 | 71 | 71 |
| MRSA 653130502 | G | G | G | G | G | G |
| MRSA 599190802 R | G | G | G | G | G | G |
| MRSA 1.1.8 | G | G | G | G | G | G |
| MRSA 5030 | LG | G | LG | G | G | G |
| MRSA ATCC 43300 | G | G | G | G | G | G |
| MRSA FOX 684 RDC 77 | LG | LG ( | LG | LG | LG | LG |
| MSSA 1.1.2 | AG | AG | AG | G (colorless) | G | AG |
| MSSA M366806 | AG | AG | AG | G | AG | AG |
| MSSA M366930 | AG | AG | AG | G | Nc | AG |
| MSSA 4007 | G | AG | AG | G | Nc | G |
| MSSA96019 | AG | G | AG | G | G | AG |
| MSSA ATCC 25923 | AG | AG | AG | AG | AG | AG |
| MSSA 3890 | AG | AG | AG | G (colorless) | AG | AG |
| MSSA 93096 | AG | AG | AG | G | AG | AG |

In control plates with CTT or CRO only, not submitted to any stress, all MRSA grew, when one strain of MSSA was able to grow at 24 h.

In plates combining UT and CRO, but not submitted to stress, all MRSA grew and no MSSA was able to grow.

All MRSA grew, and the majority of MSSA strains was also able to grow at 24 h in plates with CTT submitted to Example 3

Inhibition of Other Species

Sensitivity, specificity as well as selectivity of a medium comprising CFP+CRO+CTT was studied.

The basal medium composition was the same as described in Example 1. Abbreviations have the same meaning.

TABLE 10

Inhibition of *Staphylococcus epidermidis*

| Strains | CFP 3.5 mg/L | CRO 2 mg/L CTT 1.75 mg/L | CRO 2 mg/L CTT 1.75 mg/L CFP 0.5 mg/L | CTT 2 mg/L CPD 1.5 mg/L | CTT 2 mg/L CPD 1 mg/L CFP 1 mg/L |
|---|---|---|---|---|---|
| Experiment # | 7 | 7 | 7 | 18 | 18 |
| MRSE SDP 1589 | AG | G pinkish | G white | G pink | G white to slightly pinkish |
| MRSE SE 44476 | AG | G pinkish | Little G white | G pinkish | G less colored |
| MRSE SE 49704 | AG | G white | G white with smaller cfu | G pinkish | G less colored and smaller cfu |
| 6 strains of MRSA | 4 AG; 2 G | 6 G | 1 AG; 5 G | 1 AG; 5 G | 1 AG; 5 G |

Adding CFP in a medium containing already another cephalosporin reduces the coloration or inhibits the growth of methicillin resistant *S. epidermidis*, reducing the risk of false positive results.

Furthermore higher sensitivity and specificity was observed against MSSA and MRSE.

The claimed invention is:

1. A culture medium for screening or enrichment of methicillin-resistant *Staphylococcus aureus* (MRSA) comprising a combination of cephalosporins selected from the group consisting of cefotetan (CTT) and ceftriaxone (CRO); cefotetan (CTT) and cefpodoxime (CPD); cefsulodin (CFS) and ceftriaxone (CRO); cefsulodin (CFS) and cefepime (FEP); and cefotetan (CTT) and ceftiofur (XLN) and wherein each cephalosporin is present in a concentration of between 1.0 mg/l and 3.5 mg/l.

2. The culture medium according to claim 1, said medium further comprising a chromogenic agent.

3. The culture medium according to claim 2, wherein the chromogenic agent is 6 chloro 3-indoxyl phosphate.

4. The culture medium according to claim 1, wherein said culture medium is an agar culture medium.

5. The culture medium according to claim 1, wherein said culture medium is a broth.

6. The culture medium according to claim 1, said culture medium comprising:
 a) 1.1 to 2.5 mg/l of cefotetan and 1.5 to 2.5 mg/l of ceftriaxone;
 b) 1.75 mg/l cefotetan and 2.4 mg/l ceftriaxone; or
 c) 2.4 mg/l cefotetan and 2.4 mg/l ceftriaxone.

7. The culture medium according to claim 1, said culture medium comprising:
 2 mg/l cefotetan and 2 mg/l ceftriaxone,
 2.4 mg/l cefotetan and 2.4 mg/l ceftriaxone,
 2 mg/l cefotetan and 1.5 mg/l cefpodoxime,
 2.5 mg/l cefotetan and 1.8 mg/l cefpodoxime,
 3.5 mg/l cefsulodin and 2 mg/l ceftriaxone, or
 3 mg/l cefsulodin and 2 mg/l cefepime.

8. The culture medium according to claim 1, said culture medium further comprising cefoperazone.

9. The culture medium according to claim 8, wherein said culture medium comprising cefoperazone is at a concentration of between 0.1 mg/l to 3 mg/l.

10. The culture medium of claim 1, wherein said combination of cephalosporins is cefotetan (CTT) and ceftriaxone (CRO).

11. The culture medium of claim 1, wherein said combination of cephalosporins is cefotetan (CTT) and cefpodoxime (CPD).

12. The culture medium of claim 1, wherein said combination of cephalosporins is cefsulodin (CFS) and ceftriaxone (CRO).

13. The culture medium of claim 1, wherein said combination of cephalosporins is cefsulodin (CFS) and cefepime (FEP).

14. The culture medium of claim 1, wherein said combination of cephalosporins is cefotetan (CTT) and ceftiofur (XLN).

15. The culture medium of claim 1, wherein each cephalosporin is present in a concentration of between 1.25 mg/l and 3.5 mg/l.

16. The culture medium of claim 1, wherein each cephalosporin is present in a concentration of between 1.1 mg/l and 3.5 mg/l.

17. A method for screening or enriching methicillin-resistant *Staphylococcus aureus* (MRSA) in a culture medium, which method comprises (i) inoculating the culture medium according to claim 1, with bacteria to test, and (ii) culturing said bacteria in said culture medium.

18. The method according to claim 17, wherein the bacteria to test are in the form of a clinical sample.

19. The method according to claim 18, wherein said clinical sample is a nasal swab, a wound sample or a blood sample.

20. A method for screening or enriching methicillin-resistant *Staphylococcus aureus* (MRSA) in a culture medium, which method comprises (i) inoculating the culture medium according to claim 2, with bacteria to test, (ii) culturing said bacteria on said culture medium, and (iii) identifying the presence of MRSA strains on said culture medium.

* * * * *

UNITED STATES PATENT AND TRADEMARK OFFICE
CERTIFICATE OF CORRECTION

| | |
|---|---|
| PATENT NO. | : 9,434,978 B2 |
| APPLICATION NO. | : 13/519161 |
| DATED | : September 6, 2016 |
| INVENTOR(S) | : Christine Favier and Agnès Kammoun |

It is certified that error appears in the above-identified patent and that said Letters Patent is hereby corrected as shown below:

On the Title Page

On the title page, under abstract "20 Claims, No Drawings" should read --30 Claims, No Drawings--.

In the Specification

Column 1:
Lines 44-45, "MRSASelect" should read --MRSA*Select*--.

Column 4:
Line 4, "cefora nide," should read --ceforanide,--.
Line 16, "(CU)," should read --(CTT),--.

In the Claims

Column 20:
Line 58, after claim 20, please insert:
--21. A method for screening or enriching methicillin-resistant *Staphylococcus aureus* (MRSA) in a culture medium, which method comprises (i) inoculating the culture medium according to claim 1, with bacteria to test, and (ii) culturing said bacteria on said culture medium.

22. The method according to claim 21, said medium further comprising a chromogenic agent.

23. The method according to claim 22, wherein the chromogenic agent is 6 chloro 3-indoxyl phosphate.

24. The method according to claim 21, wherein said culture medium is an agar culture medium.

Signed and Sealed this
Tenth Day of January, 2017

Michelle K. Lee
*Director of the United States Patent and Trademark Office*

25. The method according to claim 21, said culture medium further comprising cefoperazone.

26. The method of claim 21, wherein said combination of cephalosporins is cefotetan (CTT) and ceftriaxone (CRO).

27. The method of claim 21, wherein said combination of cephalosporins is cefotetan (CTT) and cefpodoxime (CPD).

28. The method of claim 21, wherein said combination of cephalosporins is cefsulodin (CFS) and ceftriaxone (CRO).

29. The method of claim 21, wherein said combination of cephalosporins is cefsulodin (CFS) and cefepime (FEP).

30. The method of claim 21, wherein said combination of cephalosporins is cefotetan (CTT) and ceftiofur (XLN).--.